United States Patent
Virtanen

(10) Patent No.: US 7,091,034 B2
(45) Date of Patent: Aug. 15, 2006

(54) DETECTION SYSTEM FOR DISK-BASED LABORATORY AND IMPROVED OPTICAL BIO-DISC INCLUDING SAME

(75) Inventor: Jorma Virtanen, Irvine, CA (US)

(73) Assignees: Burstein Technologies, Inc., Los Angeles, CA (US); Nagaoka & Co., Ltd., Hyogo (JP)

(*) Notice: Subject to any disclaimer, the term of this patent is extended or adjusted under 35 U.S.C. 154(b) by 593 days.

(21) Appl. No.: 10/020,140

(22) Filed: Dec. 14, 2001

(65) Prior Publication Data

US 2002/0076805 A1 Jun. 20, 2002

Related U.S. Application Data

(60) Provisional application No. 60/255,845, filed on Dec. 15, 2000.

(51) Int. Cl.
*C12M 1/34* (2006.01)

(52) U.S. Cl. .............. 435/287.2; 435/287.3; 435/288.5; 435/288.7

(58) Field of Classification Search ............. 435/287.2, 435/288.5, 288.7, 91.2
See application file for complete search history.

(56) References Cited

U.S. PATENT DOCUMENTS

| | | |
|---|---|---|
| 4,898,832 A | 2/1990 | Klose et al. |
| 5,061,381 A | 10/1991 | Burd |
| 5,122,284 A | 6/1992 | Braynin et al. |
| 5,160,702 A | 11/1992 | Kopf-Sill et al. |
| 5,310,523 A | 5/1994 | Smethers et al. |
| 5,472,603 A | 12/1995 | Schembri |
| 5,545,540 A | 8/1996 | Mian |
| 5,591,643 A | 1/1997 | Schembri |
| 5,593,838 A | 1/1997 | Zanzucchi et al. |
| 5,605,662 A | 2/1997 | Heller et al. |
| 5,843,767 A | 12/1998 | Beattie |
| 6,030,581 A * | 2/2000 | Virtanen ............. 422/68.1 |
| 6,063,589 A | 5/2000 | Kellogg et al. |
| 6,117,630 A | 9/2000 | Reber et al. |
| 6,153,425 A * | 11/2000 | Kozwich et al. ......... 435/287.2 |

(Continued)

FOREIGN PATENT DOCUMENTS

DE 10037687 A1 2/2002

(Continued)

OTHER PUBLICATIONS

Schembri, et al., Centrifugation and capillarity integrated into a multiple analyte whole blood analyzer, Jour. Automatic Chemistry, 17(3):99-104 (1995).

(Continued)

*Primary Examiner*—David Redding
(74) *Attorney, Agent, or Firm*—Knobbe, Martens, Olson & Bear, LLP

(57) ABSTRACT

A detection system for use in optical disk-based devices for measuring the presence of an analyte in a sample. The detection system includes an analyte detector unit containing a primary detector which selectively reacts with analyte present in a sample to produce an amplification agent. The detection system further includes an amplification unit comprising a plurality of secondary detection agents which are each changeable between a negative and positive detection state. A fluid connection is provided between the analyte detector unit and amplification unit to provide reactive contact between the amplification agent and the plurality of detection agents. The amplification agent is capable of changing a plurality of detection agents between the negative and positive detection states to thereby amplify the measurable presence of the analyte.

8 Claims, 10 Drawing Sheets

U.S. PATENT DOCUMENTS

| | | |
|---|---|---|
| 6,342,349 B1 * | 1/2002 | Virtanen ........................ 435/6 |
| 6,506,594 B1 * | 1/2003 | Barany et al. ........... 435/287.2 |
| 2001/0055821 A1 | 12/2001 | Mian et al. |
| 2002/0098528 A1 | 7/2002 | Gordon et al. |
| 2002/0106786 A1 | 8/2002 | Carvalho et al. |
| 2002/0150512 A1 | 10/2002 | Kellogg et al. |
| 2002/0163642 A1 | 11/2002 | Zoval et al. |
| 2002/0171838 A1 | 11/2002 | Pal et al. |
| 2002/0196435 A1 | 12/2002 | Cohen et al. |
| 2003/0003464 A1 | 1/2003 | Phan et al. |

FOREIGN PATENT DOCUMENTS

| | | |
|---|---|---|
| EP | 0297394 A2 | 1/1989 |
| EP | 0392475 A2 | 10/1990 |
| EP | 0417305 A1 | 3/1991 |
| EP | 0504432 A1 | 9/1992 |
| EP | 0693560 A2 | 1/1996 |
| EP | 0608006 B1 | 3/1999 |
| WO | WO 93/22053 | 11/1993 |
| WO | WO 95/33986 | 12/1995 |
| WO | WO 96/045747 | 2/1996 |
| WO | WO 97/21090 | 6/1997 |
| WO | WO 98/07019 | 2/1998 |
| WO | WO 98/12559 | 3/1998 |
| WO | WO 98/32535 | 7/1998 |
| WO | WO 98/38510 | 9/1998 |
| WO | WO 98/45693 | 10/1998 |
| WO | WO 98/53311 | 11/1998 |
| WO | WO 99/58245 | 11/1999 |
| WO | WO 00/05582 | 2/2000 |
| WO | WO 00/26677 | 5/2000 |
| WO | WO 00/78455 A1 | 12/2000 |
| WO | WO 01/02737 A1 | 1/2001 |
| WO | WO 01/43938 A1 | 6/2001 |
| WO | WO 01/44875 A2 | 6/2001 |
| WO | WO 01/46465 A2 | 6/2001 |
| WO | WO 01/47637 A1 | 7/2001 |
| WO | WO 01/47638 A2 | 7/2001 |
| WO | WO 01/87485 A2 | 11/2001 |
| WO | WO 01/87486 A2 | 11/2001 |
| WO | WO 01/87487 A2 | 11/2001 |
| WO | WO 01/87768 A2 | 11/2001 |
| WO | WO 02/42498 A2 | 5/2002 |

OTHER PUBLICATIONS

Pfahler, Liquid Transport in Micron and Submicron Size Channels: A Dissertation in Mechanical Engineering and Applied Mechanics, (1992).

Duffy, et al., Microfabricated Centrifugal Microfluidic Systems: Characterization and Multiple Enzymatic Assays, J. Anal. Chem., 71(20):4669-4678, (1999).

* cited by examiner

DETECTION SYSTEM FOR DISK-BASED LABORATORY AND IMPROVED OPTICAL BIO-DISC INCLUDING SAME

CROSS REFERENCE TO RELATED APPLICATION

This application claims priority from U.S. Provisional Application Ser. No. 60/255,845, filed Dec. 15, 2000, which is incorporated herein by reference in its entirety.

BACKGROUND OF THE INVENTION

1. Field of the Invention

The present invention relates generally to analytical devices which are located on an optical disk, such as a compact disk (CD) or digital video disk (DVD). More particularly, the present invention relates to optical bio-discs including detection systems which form a part of such disk-based analytical devices.

2. Description of Related Art

Clinical chemistry involves the qualitative and quantitative analyses of body fluids, such as blood, urine and spinal fluid, as well as feces, calculi and other materials. Traditionally, clinical laboratories have been centrally located operations which utilized large and expensive automated equipment to run a multitude of different tests on large numbers of samples. A major problem with such centralized testing laboratories was and continues to be that the samples must be transported from doctors' offices and hospitals to the central laboratory. Transporting of biological samples is time consuming, costly and may result in the deterioration of the sample when it is not properly preserved.

The majority of automated analytical equipment which have been used in centrally located clinical laboratories require a relatively large amount of sample which is aspirated into the analyzer and split into a number of aliquots. Reagents required for each different assay are also aspirated into the analyzer. The various aliquots of sample and reagents are pumped via a peristaltic pump through complex arrangements of tubes and reaction chambers to achieve the desired chemical reactions. One or more skilled technicians are required to run the analyzer and constantly monitor the pumping system to insure that samples and reagents are flowing properly through the system. Constant maintenance of these large and complex analyzers is essential to insure that none of the multitude of tubes and passageways become blocked.

More recently, there has been a trend towards decentralization where the majority of routine clinical chemistry testing is done on smaller instruments which are located in the doctors office or hospital. A host of small analyzers have been developed which rely on centrifugal force to move samples and reagents through the analytical system. These units are well-suited for use in hospital laboratories and doctors offices because they eliminate the complexities associated with the larger pump driven autoanalyzers. These rotor or centrifuge based systems are stand alone units which tend to be expensive and require at least some training to operate. Accordingly, they have been limited to use in hospitals and doctors offices.

An even more recent development has been the discovery that optical disks, such as CD's and DVD's can be utilized as platforms for performing centrifuge-based analytical chemistry. In addition to functioning as a centrifuge, the optical disk can store information which can be used to control the analytical procedure. Further, the laser used in all CD and DVD players provides an especially useful built-in optical detector system. These laboratories on a disk are described in International Publication Number: W098/38510. The optical disk based analytical devices are extremely versatile and can be used by anyone who has access to a personal computer which includes a CD or DVD unit.

A feature of optical disk-based analytical devices is that they require relatively small amounts of blood or other sample fluid. This is desirable since there has been a continuing push in clinical chemistry to develop analytical devices which use smaller and smaller amounts of sample material. Sample size becomes especially critical in newborn babies and the elderly. However, as sample size decreases, the number of analyte molecules present in the sample also decreases. For extremely small samples, the number of analyte molecules which may be present can be on the order of a few hundred. In addition, there are situations where it is desirable to detect extremely low concentrations of analyte in a sample. As a result, there is a need to provide detection systems for optical disk-based analytical devices which are capable of detecting extremely small amounts of analyte in an accurate and reproducible manner.

SUMMARY OF THE INVENTION

In accordance with the present invention, a detection system is provided for use in optical disk-based analytical devices to measure the presence of small amounts of analytes in a sample. The invention is based on the use of cascading chemical reactions to amplify a single interaction between an analyte molecule and a primary detector into a change of multiple detection agents between negative and positive detection states. The invention is particularly well adapted for use with optical disk-based devices which employ microfluidic systems.

The detection system of the present invention includes an analyte detector unit or zone in which a primary detector is located. The primary detector is designed to selectively react with any analyte present in a sample to produce an amplification agent. The system further includes an amplification zone or unit. Secondary detection agents are located within the amplification unit. The detection agents are changeable between negative and positive detection states. A fluid connection is provided between the analyte detector unit and the amplification unit so that the amplification agent released in the analyte detector unit can be transported into the amplification unit for interaction with the detection agents. As a feature of the present invention, each amplification agent is capable of changing a plurality of the detection agents between their negative and positive detection states. In this way, a single analyte molecule is capable of releasing an amplification agent which in turn controls the detection state of numerous detection agents.

As a further feature of the present invention, intermediate amplification zones or units are provided wherein intermediary multiplier agents are produced which further contribute to the chemical cascade which is initiated by the initial release of the primary amplification agent.

The detection system in accordance with the present invention is especially well suited for measuring the presence of analyte in samples on a molecular scale. Samples on the order of a few microliters can be tested wherein only a few analyte molecules react with the primary detector to release a few amplification agents. The amplification agents are then transferred to the amplification unit where they enzymatically or catalytically convert a multitude of detection agent molecules from a negative to positive detection state. The detection state of the detection agents can then measure accurately utilizing the laser beam which forms part of every CD or DVD player.

The above described and many other features and attendant advantages of the present invention will become better understood by reference to the following detailed description when taken in conjunction with the accompanying drawings.

DETAILED DESCRIPTION OF THE INVENTION

The detection systems in accordance with the present invention may be used in a wide variety of optical disk-based analytical devices. The invention is especially well suited for use in analytic devices of the type described in International application which was published on Sep. 3, 1998, under International Publication No. WO 98/38510.

The size of the conduits, separation zones and assay chambers can be any size which is suitable for use in disk-based analytical systems. However, the optical bio-disc of the present invention is particularly applicable to microfluidic assay systems which are designed to test extremely small quantities of sample and which use equally small amounts of reagents. Microfluidic systems are generally considered to be those in which the reaction and preparation chambers, as well as the conduits connecting the various reaction zones or units are on the order of a few nanometers up to a few hundred microns.

The sample amounts which are amenable to testing in microfluidic systems are on the order of a few microliters up to a few hundred microliters. An optical disk (CD or DVD) on which the detection system of the present invention is located is shown generally at 10 in FIGS. 1–3. The disk 10 is a conventional or modified CD or DVD in which various microfluidic reaction chambers and connecting channels are etched. It is preferred that the disk include a sample assay section 12 and a software section 14, as shown in FIG. 3. The software section interacts with the optical reader unit to control the sample assay. The operation and interaction between the optical reader and disk is described in detail in publication WO 98/38510, the contents of which is hereby incorporated by reference.

Figure 1:
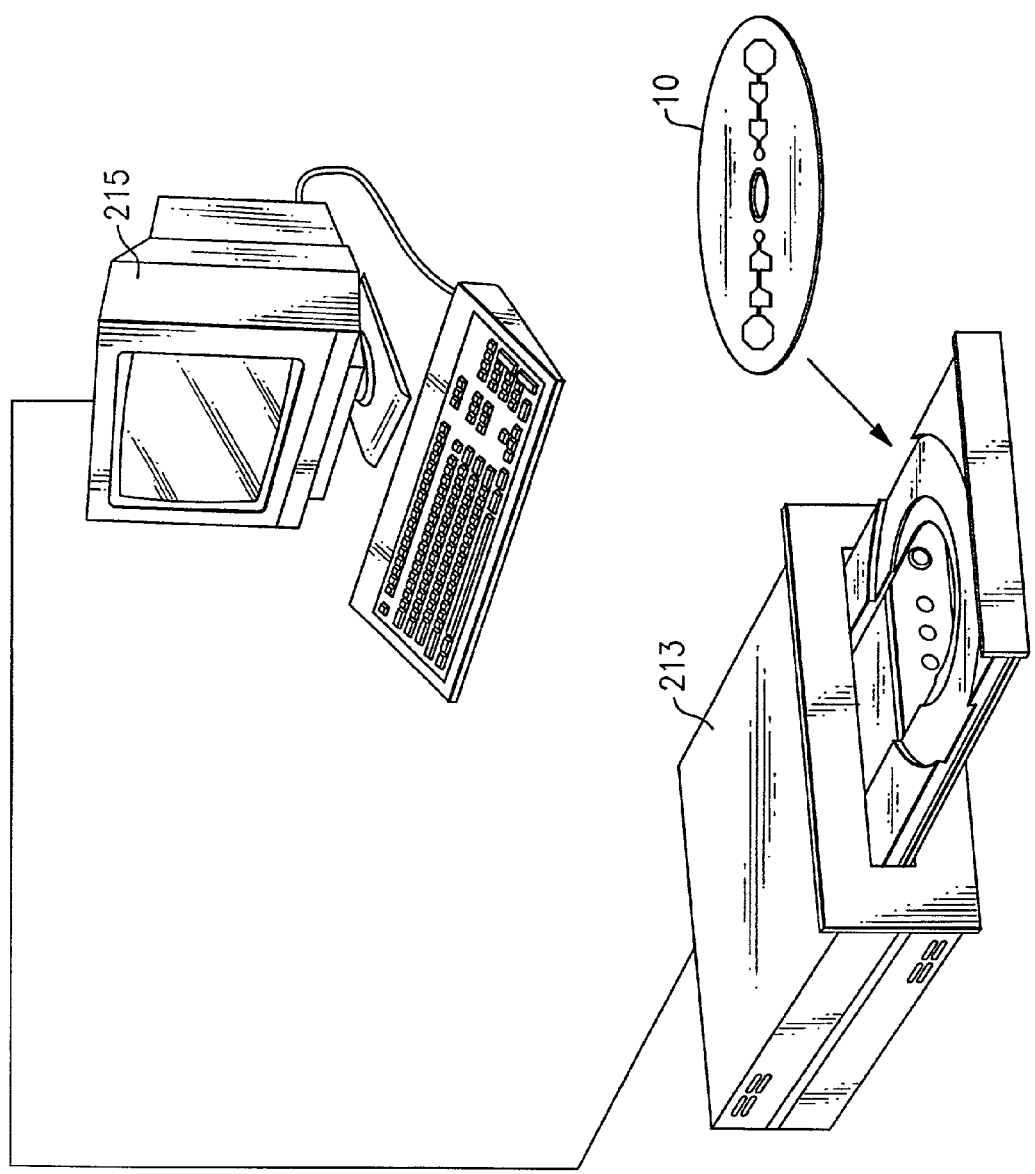
FIG. 1 is a perspective view of a disc drive and monitor used in conjunction with the optical bio-disc detection system of the present invention.
Figure 2:
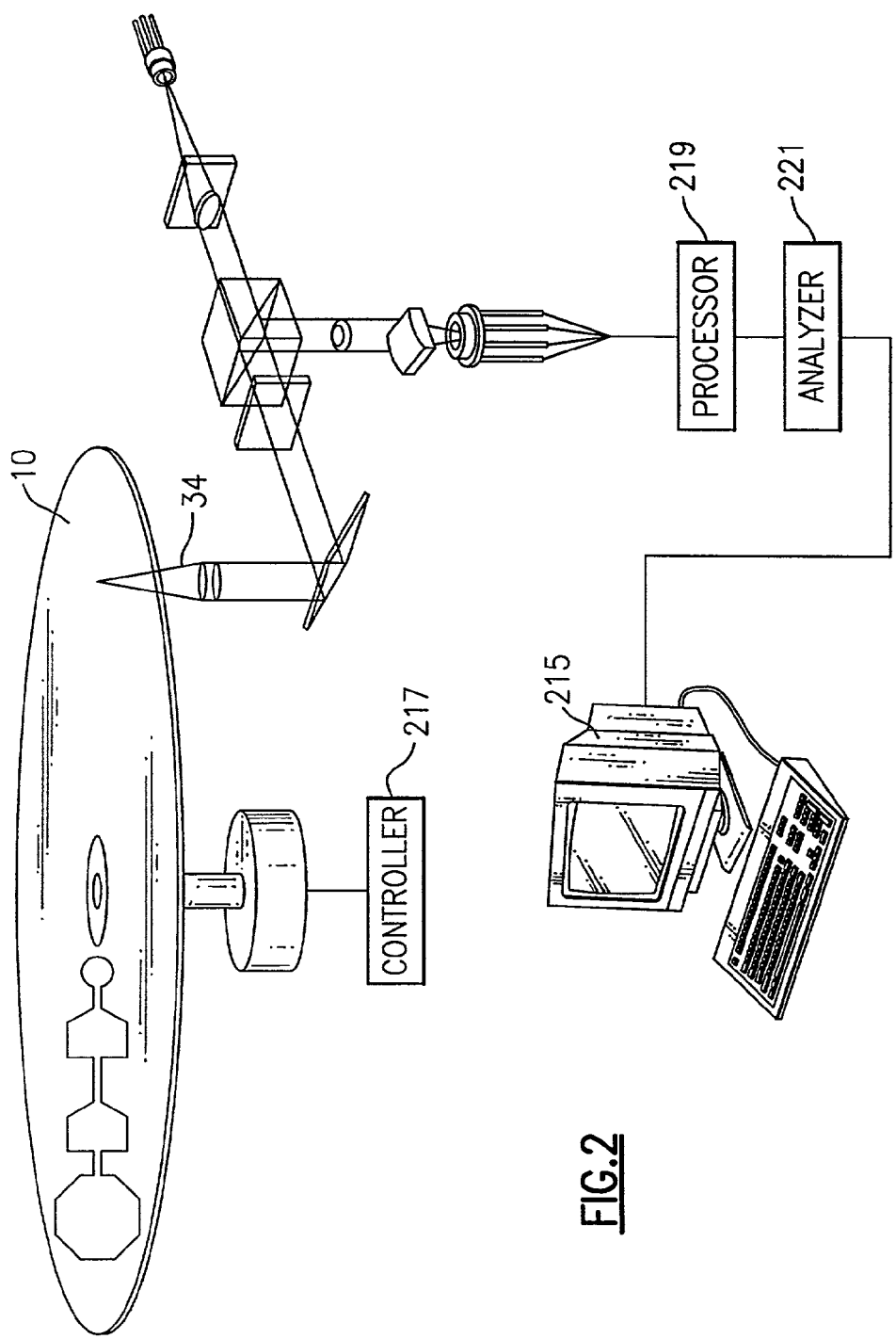
FIG. 2 is a more detailed pictorial representation of the disc drive, monitor, and optical bio-disc shown in FIG. 1.
Figure 3:
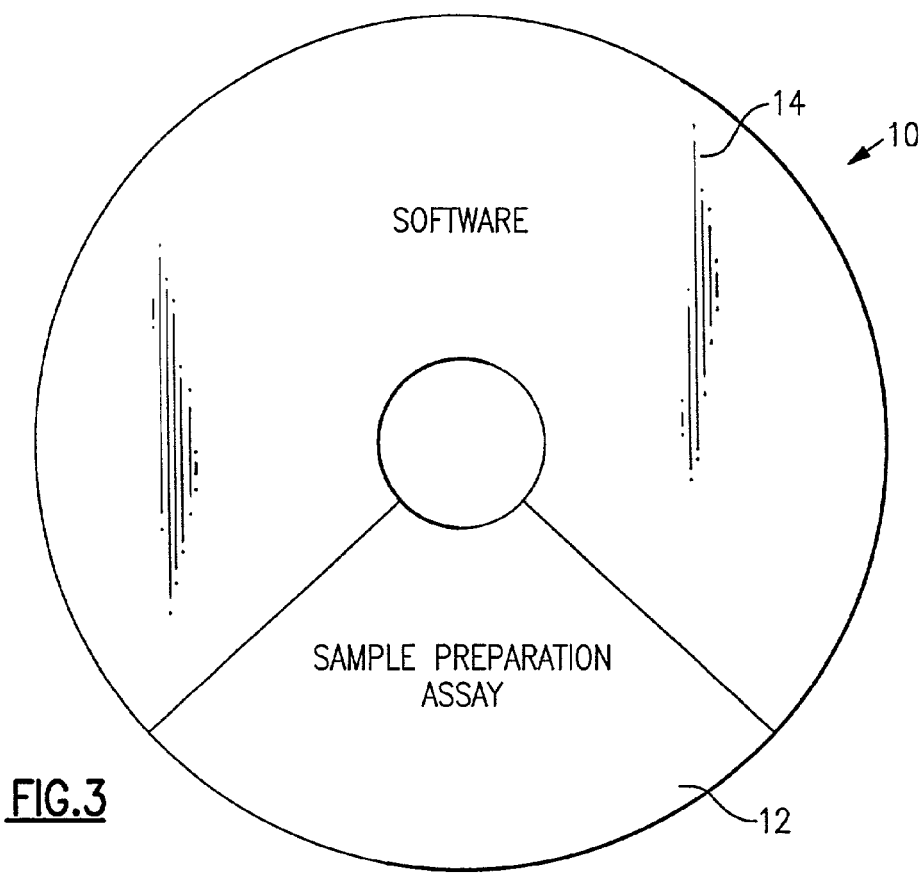
FIG. 3 is a diagrammatic representation of a CD or DVD disk on which the detection system of the present invention is placed.

Referring now to FIGS. 1 and 2, the optical bio-disc 10 of the present invention is employed in conjunction with a disc drive 213 and a display monitor 215. As illustrated in FIG. 2, the disc drive 213 includes a controller 217 for rotating the disc 10 in a predetermined manner. The disc drive 213 also includes a processor 219 and an analyzer 221 which are employed to read, write, and analyze information associated with the disc 10 and display desired results on the monitor 215.

Figure 4:
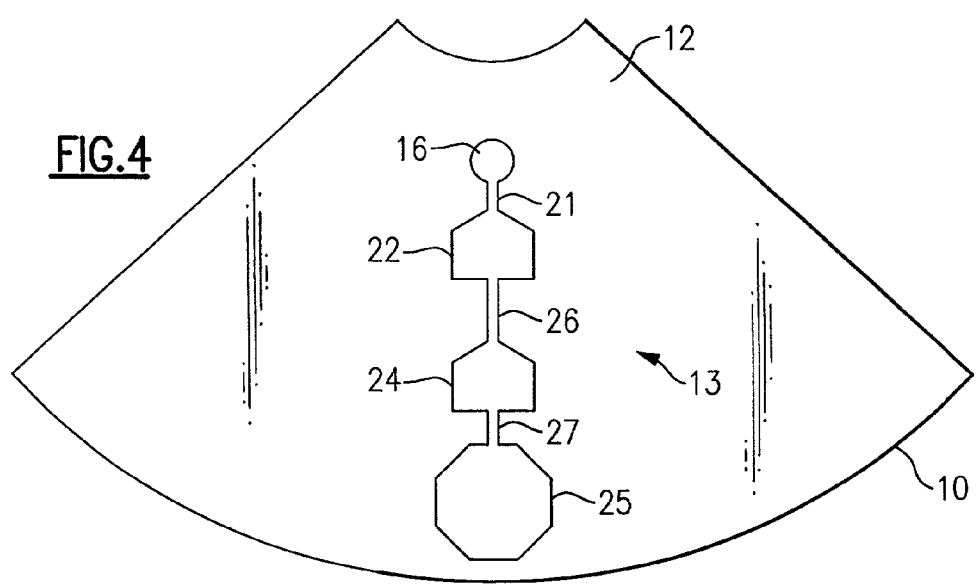
FIG. 4 is a further diagrammatic view of the disk shown in FIG. 3 wherein a basic exemplary detection system is diagrammatically shown.

A diagrammatic view of the assay portion of disk 10 is shown in FIG. 4. A simplified and enlarged analytical system is shown generally at 13. The system 13 includes a sample inlet 16 which is connected to an analyte detector unit or zone 22 by way of a microfluidic conduit 21. An amplification unit or zone 24 is connected to the analyte conduit 26. A waste/overflow chamber 25 is connected to the amplification unit 24 by way of microconduit 27. The assay system depicted in FIG. 4 is enlarged and shown out of proportion for explanatory purposes. The detection system in accordance with the present invention can be used in combination with any number of sample preparation and sample separation systems. The principal purpose of the present invention is to amplify the reaction which measures the presence of an analyte. Accordingly, the analytical systems shown in the Figures have been simplified in order to more clearly describe the invention. The additional conduits, sample separation zones, reagents and other elements required to carry out various assays are not shown since these elements will vary widely depending upon the particular analyte being tested. Examples of such additional assay elements are described in WO 98/38510.

Figure 5A:
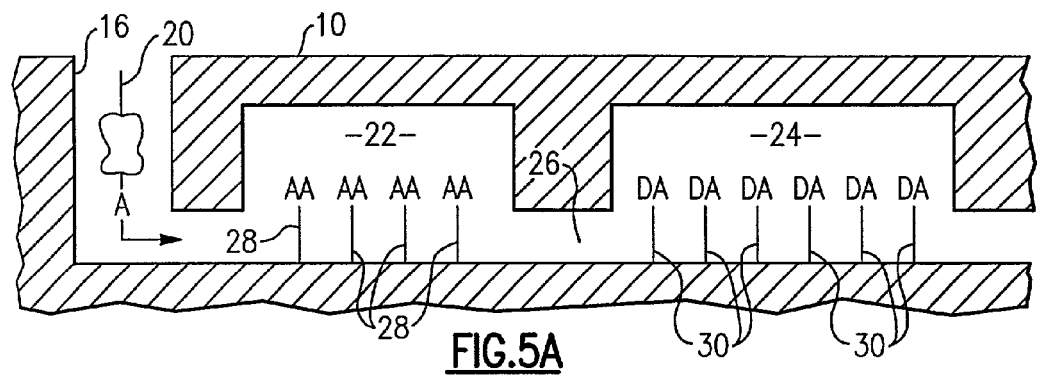
FIGS. 5A–5D are schematic side view representations of an exemplary detection system in accordance with the present invention.
Figure 5B:
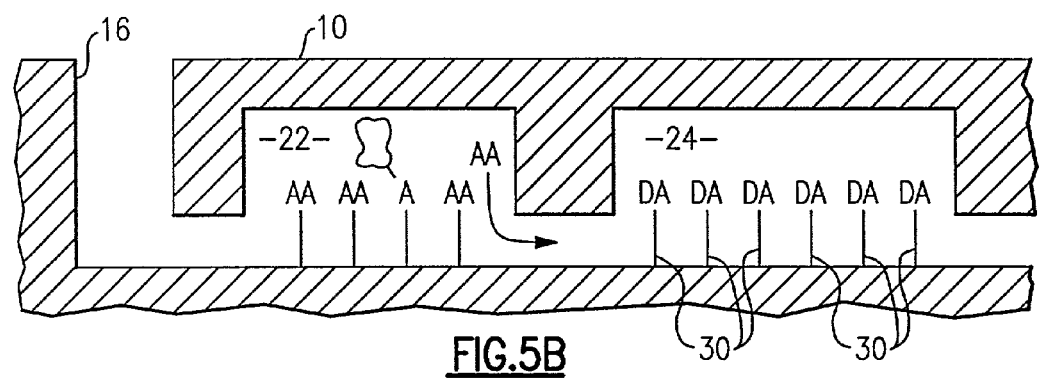
Figure 5C:
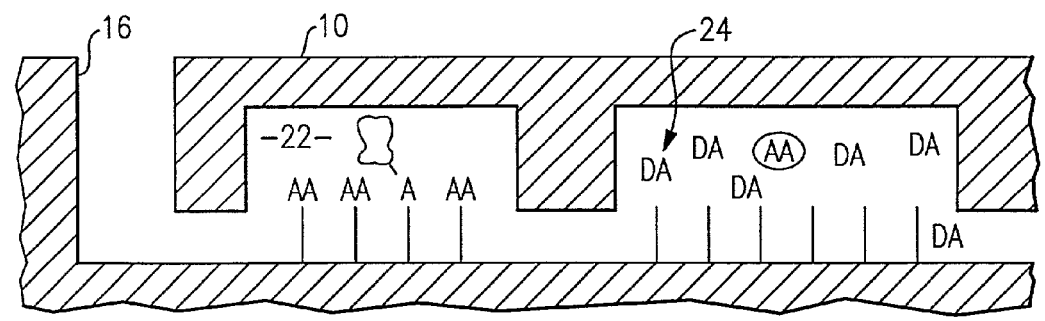

A diagrammatic side-view representation of the exemplary detection system 13 is shown in FIGS. 5A–5D. Referring to FIG. 5A, a sample 20 which includes an analyte A is introduced into the system through the sample inlet 16. It should be noted that although the various units or zones of the present system are shown diagrammatically as separated, it is possible to combine the zones or units together into a single reaction chamber, if desired. The analyte detector unit 22 includes an amplification agent (AA) which is bound to the disk as represented by lines 28. The amplification agent is an enzyme or other catalytic compound which is capable of initiating and/or controlling numerous chemical reactions. The amplification unit or zone 24 includes secondary detection agents (DA) which are chemically changeable between a negative detection state and a positive detection state. The detection agents typically will include a cleavable bond which is represented in FIG. 5A at 30.

The amplification agent (AA) along with the bond element 28 form a primary detector which must be capable of selectively reacting with the analyte. The selective reaction of the primary detector releases the amplification agent. This process is shown schematically in FIG. 5B wherein the analyte A has interacted with one of the many primary detectors present in the analyte detector unit 22. The reaction of analyte A with the primary detector releases amplification AA which then is washed or otherwise transported through the microfluidic connection 26 into the amplification unit 24. In the particular embodiment shown in FIG. 5, the amplification agent is an enzyme or other catalytic compound which is capable of cleaving the bonds 30 which hold the detection agents in place within the amplification unit 24. The cleavage and release of the detection agents is shown schematically in FIG. 5C.

Figure 5D:
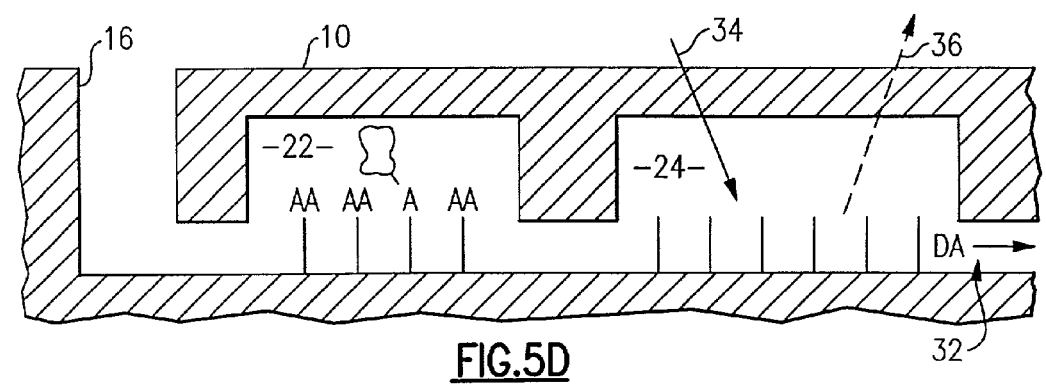

Once the detection agents have been released, they are washed to the waste container 25 from the amplification unit as shown at 32 in FIG. 5D. Once the free detection agent has been removed from the amplification unit 24, a light source, such as a laser beam 34 is directed into the amplification unit or zone 24. The reflectance from beam 34 is represented by phantom line 36 which provides a measure of the presence or absence of the detection agents. As can be seen from FIGS. 5A–5D, the single interaction of an analyte molecule with a single primary detector results in the release of multiple detection agents. This cascading process provides a significant amplification of the single initial chemical reaction between the analyte A and the primary detector.

The detection system shown in FIGS. 5A–5D involves detection agents wherein the positive detection state requires that the detection agent be cleaved from a bound position and removed from the amplification unit 24. In other words, a positive test result is achieved by measuring the absence of detection agent while a negative test result is achieved when the detection agent remains bound and present within the detection unit 24.

Figure 6A:
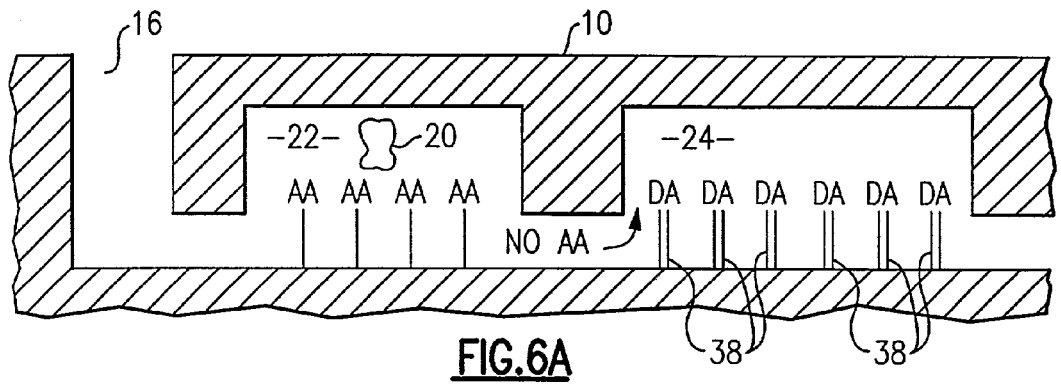
FIGS. 6A–6D are side diagrammatic views of another exemplary detection system in accordance with the present invention.

An alternate embodiment of a detection system in accordance with the present invention is shown in FIGS. 6A–6D wherein a positive test result is achieved when the detection agent remains bound within the detection unit while a negative test result is achieved when the detection agent is cleaved and removed. Specifically, an example of a negative test result is shown schematically in FIGS. 6A and 6B. In FIG. 6a, a sample 20 lacking analyte A results in no amplification agents AA being released from the detector unit 22. In this particular embodiment, the secondary detection agents include a detection agent (DA) which is bound to the disk by way of a cleavable bond 38. When amplification agent is introduced into contact with the secondary detection agents, the cleavable bonds 38 are rendered non-cleavable.

Figure 6B:
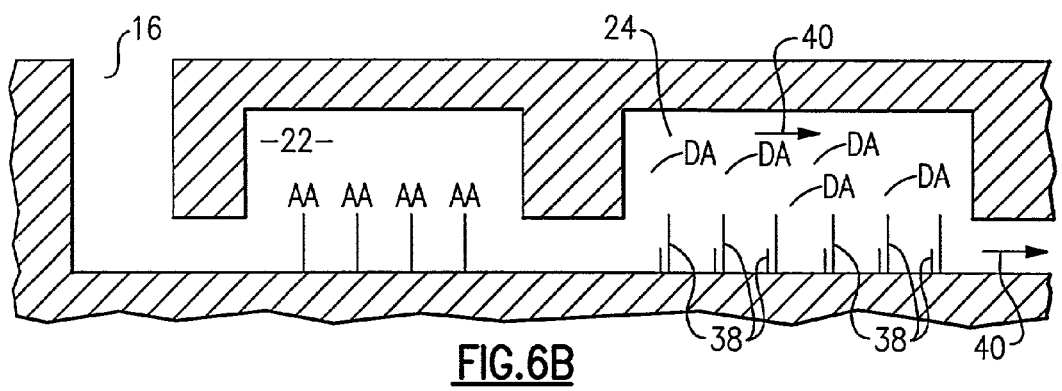

Referring to FIG. 6B, the test procedure next involves introducing a reagent into the amplification unit 24 which cleaves all bonds 38 which have not been rendered uncleavable by action of the amplification agent. The cleaved detection agents are washed from the amplification unit 24 as represented by arrows 40. A laser beam is then used to detect the absence of the detector agents in amplification unit 24 to thereby provide a negative test result.

Figure 6C:
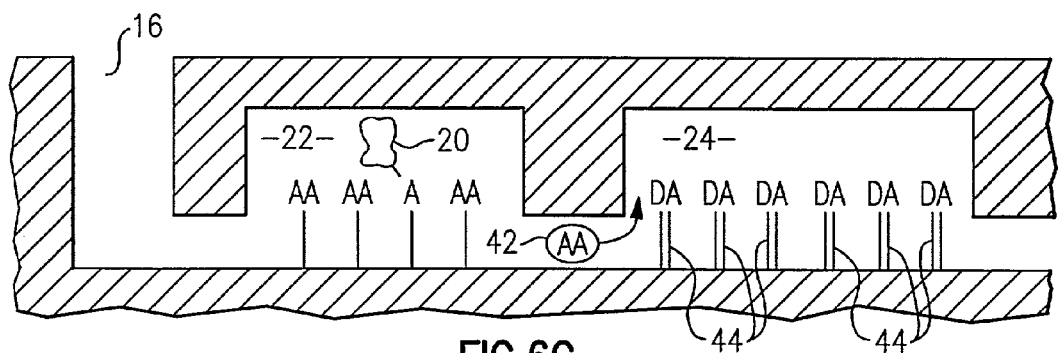
Figure 6D:
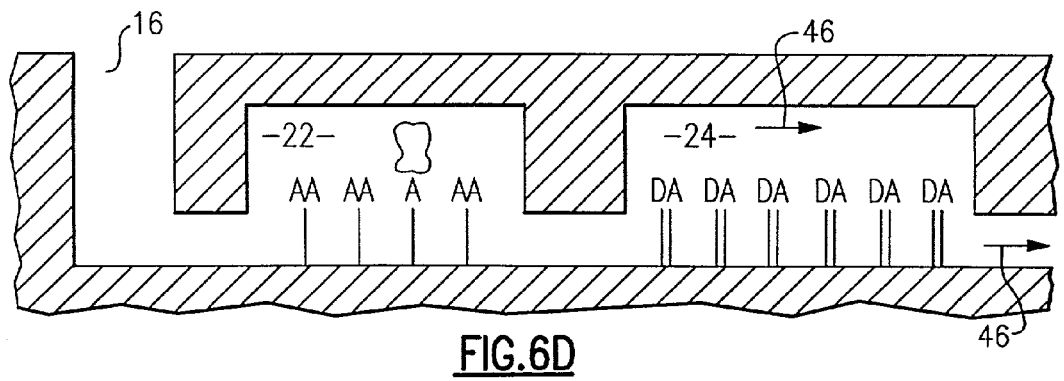

A positive test result is shown in FIGS. 6C and 6D. In FIG. 6C, a sample 20 having analyte A is shown selectively bound to a primary detector with the resultant release of an amplification agent as shown at 42. The amplification agent travels into the amplification unit 24 where it catalytically converts all of the cleavable bonds 38 into a non-cleavable bond 44. As shown in FIG. 6D, the amplification unit 24 is washed as indicated by arrows 46 with the same cleavage reagent used in FIG. 6B. Since the bonds have all been rendered non-cleavable, the detection agents remain within the amplification unit 24 where they are detected by a laser beam or other suitable detection system. The continued presence of the detection agents in the amplification unit 24 provides a positive test result.

The above test systems described in FIGS. 5A–5D and FIGS. 6A–6D are intended to be generic in nature since a wide variety of amplification agents and detection agents may be utilized in order to achieve the desired amplification of the initial analyte reaction. The intended result in both systems which is achieved in accordance with the present invention is that a single analyte molecule triggers a series of cascading chemical events which results in the amplification of a measurable detection agent.

Figure 7:
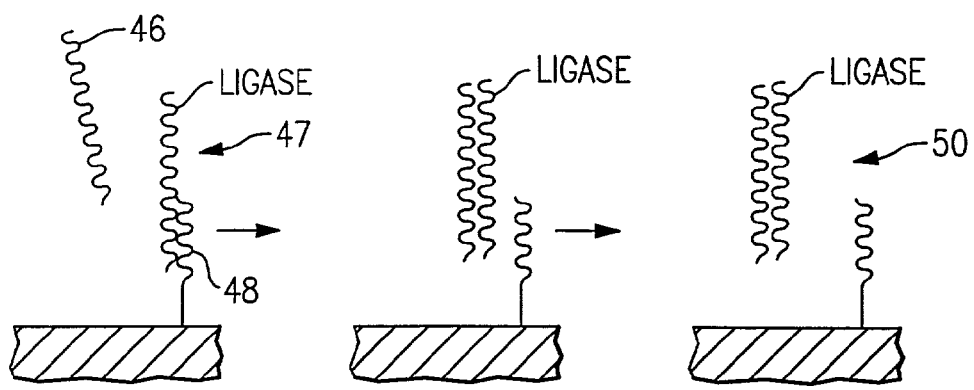
FIG. 7 is a schematic representation of an exemplary analyte detector unit wherein ligase is released as an amplification agent (AA).

FIGS. 7 and 8 provide a more detailed representation of the exemplary detection system shown in FIGS. 6A–6D. This system is based on the use of a DNA ligase as the amplification agent and a detection agent which is bound cleavably to the disk by way of a cleavable DNA bond. Referring to FIG. 7, the analyte A is a DNA molecule 46. The amplification agent is DNA ligase which has been linked to a DNA segment which is capable of hybridizing with the analyte DNA 46. The DNA-ligase is bound to the disk via a complementary DNA segment as shown at 48. The DNA analyte 46 hybridizes with the amplification agent which results in release of the ligase from the bound DNA as shown generally at 50 in FIG. 7. The DNA ligase is then washed or otherwise transported into the amplification unit 24.

Figure 8A:
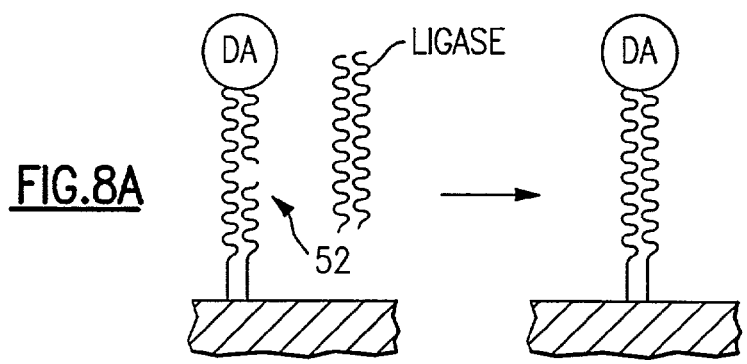
FIGS. 8A and 8B are schematic representations of an amplification unit in accordance with the present invention wherein multiple detection agents (DA) are changed to a positive detection state by the ligase enzyme.
Figure 8B:
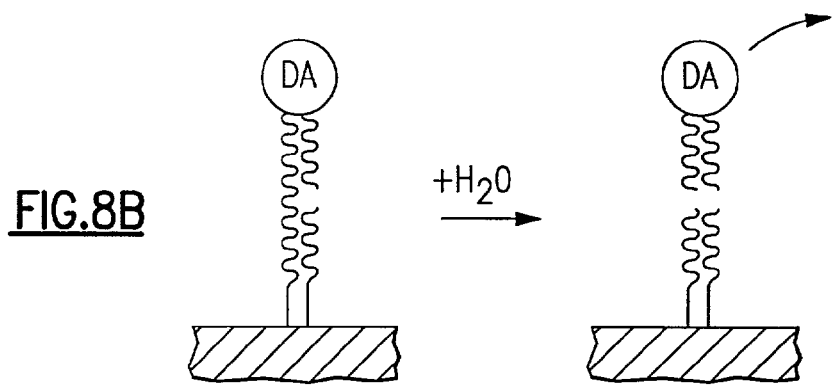

FIG. 8A shows the detection agent which is present in the amplification unit 24. The detection agent is bound to the disk by way of a cleavable DNA bond. The DNA bond is rendered cleavable by providing a nick in one of the DNA chains as shown at 52. As is well known, DNA ligase is capable of ligating nicks in multiple DNA chains. Accordingly, the ligase which is selectively released in the initial detection step is capable of securing numerous detection agents to the amplification unit 24. The detection agents therefore remain within the detection units even after the detection unit or zone 24 is washed with a cleavage reagent. It is known that small DNA segments having a single nick therein are stable in salt solutions. However, treatment of such nicked DNA segments with water results in cleavage. Accordingly, as shown in FIG. 8B, the cleavage and removal of detection agents which have not been ligated is a simple matter of washing the amplification unit with water. When analyte is not present, the detection agents are cleaved and removed from the amplification unit. When an amplification agent (i.e., ligase) is produced and present in the amplification unit, the detection agents remain bound to the disk and are not removed during washing with water.

Figure 9:
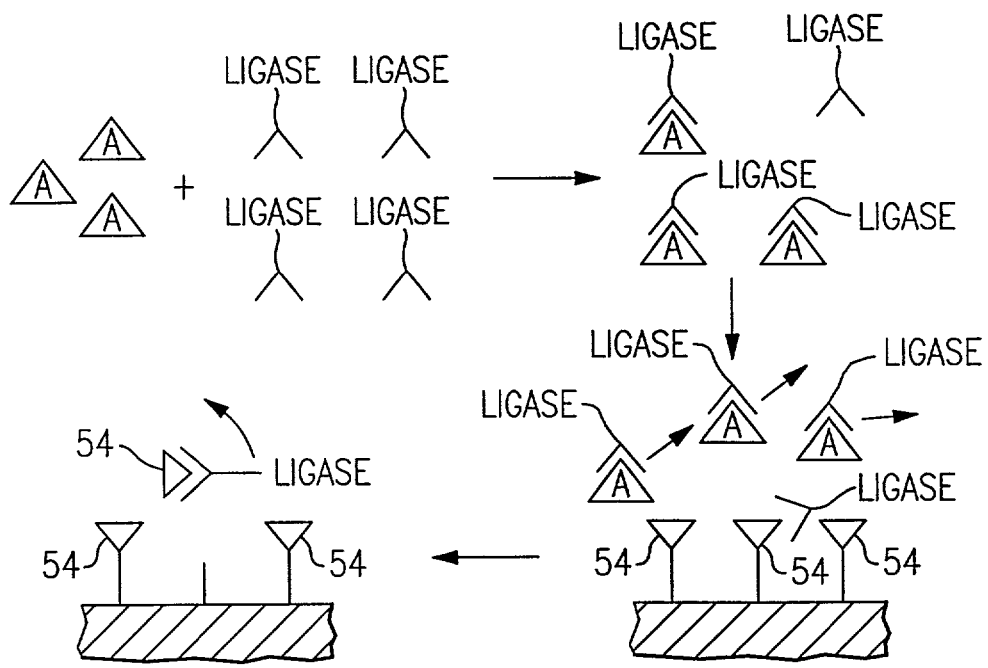
FIG. 9 is a diagrammatic representation of an additional embodiment of the present invention wherein the analyte is an antigen.

The above example was directed toward measuring DNA analytes. The present invention is also applicable to amplifying analyte reactions wherein the analyte is an antigen or antibody. As shown in FIG. 9, a sample which includes antigens A is combined with a known amount of antibody which is linked to DNA ligase. As is well known in immunochemical testing procedures, the amount of antibody which does not react with antigen in the sample is measured to provide an indirect measurement of the amount of antigen present in the sample. This is represented in FIG. 9 in the upper right hand corner wherein a single antibody linked DNA ligase molecule is left unreacted with antigen molecules. In accordance with the present invention, an amplification agent is produced by providing antigens 54 which are bound to the analyte detector unit. The unbound antibody-DNA ligase molecule selectively binds with antigen 54. The unbound antigen-antibody complexes are removed from the detector unit so that the only ligase remaining in the detector unit is that which is bound to antigen 54 as shown in the lower right hand corner of FIG. 9. The detection unit is then treated with a cleavage reagent which cleaves the antigen-antibody-ligase complex as shown in the lower left hand side of FIG. 9. This released ligase complex then functions as an amplification agent in accordance with the general scheme set forth in FIGS. 6A–6D.

Figure 10:
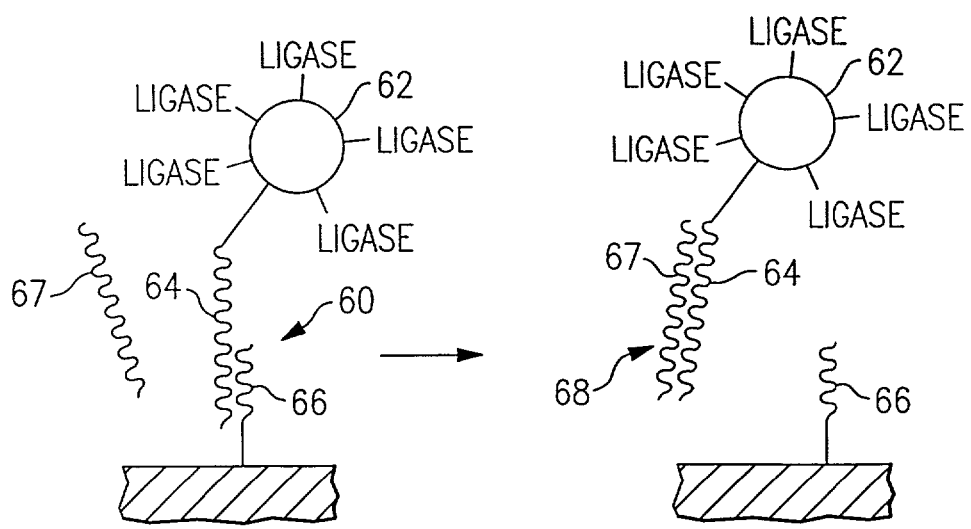
FIG. 10 is a diagrammatic representation of an analyte detector unit in accordance with the bio-disc of the present invention wherein a single analyte interaction releases multiple amplification agents.

Another embodiment of a primary detector is shown in FIG. 10 at 60. The primary detector includes an amplification agent 62 which is a small bead on which multiple ligase enzymes are bound. The beads range in size from a few nanometers to up to 100 nanometers. The beads are made from any suitable material to which enzymes may be coupled. The coupling chemistry and various other aspects of attaching enzymes to the surfaces of small beads are well known. The amplification agent 62 is coupled to an oligonucleotide 64 which is in turn coupled to a complimentary DNA segment 66 which is bound to the surface of the disk. The amplification agent 60 operates in the same manner as the amplification agent 47 shown in FIG. 7 with the principal difference being that the bead 62 provides a method for releasing multiple ligase molecules as a result of a single analyte-primary detector interaction. As shown in the right side of FIG. 10, the DNA analyte of interest 67 selectively hybridizes with the oligonucleotide 64 which results in cleavage of the amplification agent from the disk surface. The amplification agent 62 along with the DNA tail 68 is then transported to the amplification zone or unit to provide ligation of nicked oligonucleotides in the same manner as previously described in FIGS. 8A and 8B.

The preceding description of the present invention has been limited to describing situations where the amplification agent interacts directly with a plurality of secondary detection agents to change the detection agents between a negative and positive detection state and vice versa. It is also contemplated within the invention that the initial analyte-primary detector reaction be amplified a number of times in intermediate multiplier zones or units located between the initial analyte detector unit and amplification unit. This type of detection system in accordance with the present invention is shown schematically in FIGS. 11A–11D. The system is preferably located in a compact disk or DVD 110. The disc 110 may be of a conventional type or modified as needed to interact with the disc drive 213. The sample containing analyte A is introduced through inlet 116 and travels through microconduit 117 to the amplification unit 122. The detection system further includes a multiplier zone or unit 123 and an amplification unit or zone 124.

Figure 11A:
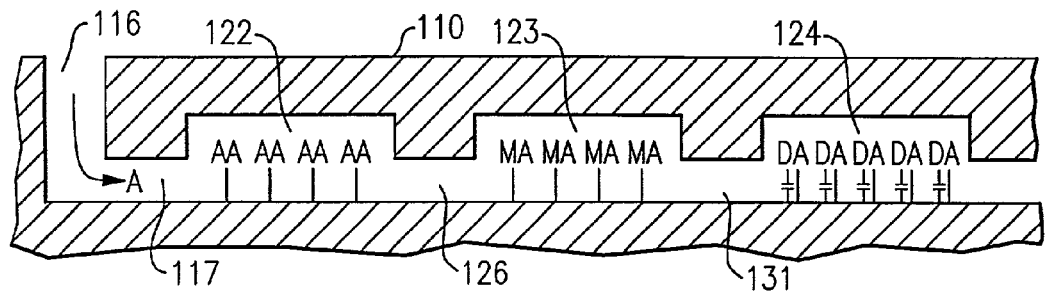
FIGS. 11A–11D are side view schematic representations of an exemplary detection system in accordance with the present invention wherein an amplification unit is provided to increase the detector amplification.
Figure 11B:
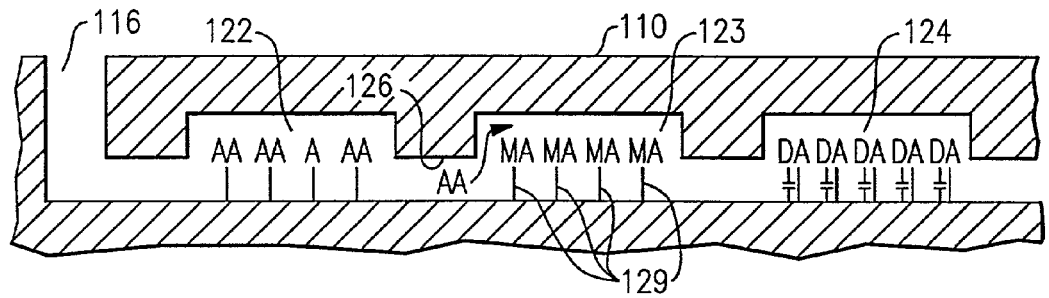
Figure 11C:
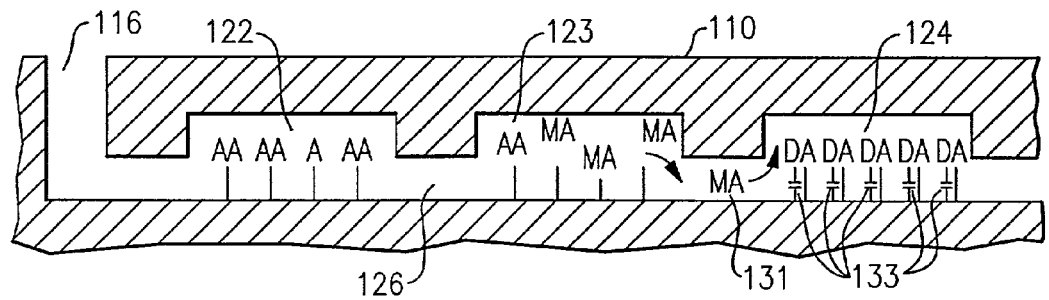

As shown in FIG. 11B, the analyte A reacts selectively with a primary detector located in detector unit 122 to release an amplification agent (AA) which is transported through microconduit 126 into the multiplier unit 123. The amplification agent is an enzyme or other catalytic molecule which is capable of cleaving the plurality of intermediary multiplier agents (MA) which would otherwise remain bound to the disk by way of bond 129. As shown in FIG. 11C, the released multiplier agents are then transported through microconduit 131 to the amplification unit 124. The detection agents (DA) are bound within the amplification unit in the same manner as the detection system described in FIGS. 6A–6D and FIGS. 8A–8B. The nicks in one of the oligonucleotides which bind the detection agent to the disk are shown schematically in FIG. 11D at 133.

Figure 11D:
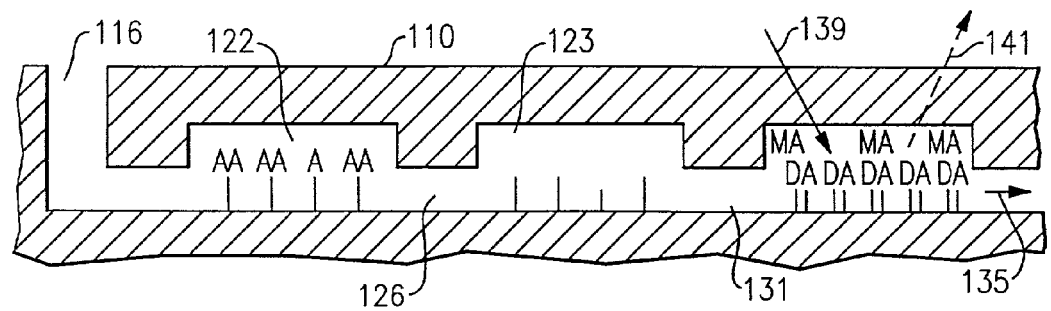

After the multiplier agents have enzymatically or catalytically bound the detection agents to the disk, the disk is washed with a cleavage reagent as represented in FIG.11D by arrow 135 to cleave and remove any detection agent which has not been bound to the disk. In this particular situation, a single analyte molecule has initiated a cascade reaction wherein the single catalyst or enzyme (AA) produces multiple enzymes (MA) which in turn act on the detection agents (DA). Once washing is complete, the presence of the detection agents is determined by the optical reader of the disk player as represented by lines 139 and 141. This particular embodiment of the present invention is particularly well suited for those situations wherein extremely small numbers of analyte molecules are present in any given sample. In such situations, the additional amplification provided by the multiplier agents is helpful in increasing a small number of analyte interactions into a measurable quantity.

Figure 12:
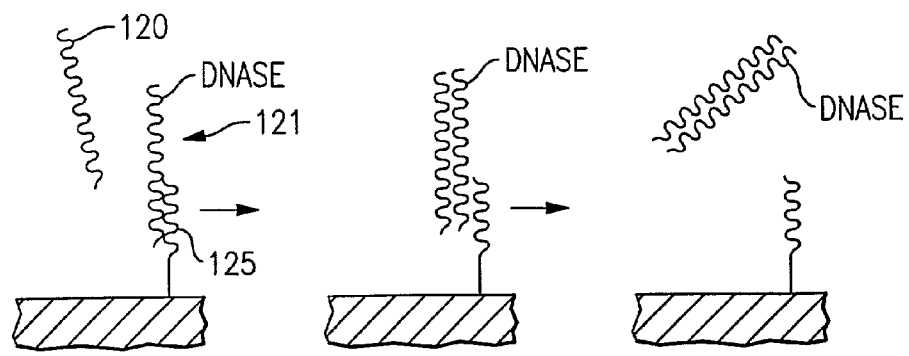
FIG. 12 is a schematic representation of a detection unit for use in the system described in FIGS. 11A–11D.

In FIG. 12, an exemplary interaction between an analyte and amplification agents for the detection system shown in FIGS. 11A–11D is depicted. An oligonucleotide analyte 120 hybridizes with an oligonucleotide 121 to which is coupled to Dnase enzyme. The oligonucleotide 121 is bound to the disk by way of a complementary oligonucleotide 125. The hybridization of the oligonucleotide analyte 120 to the oligonucleotide 121 results in the release of the Dnase. The Dnase then is transported to the multiplier zone or unit 123 where it cleaves ligase enzymes which are bound to the disk surface via an oligonucleotide linkage. This step of releasing ligase multiplier agents is shown diagrammatically in FIG. 13. The multiple ligase agents which are released by a single Dnase are then transported to the amplification unit 124 where each individual ligase is capable of ligating numerous nicked oligonucleotides to provide secure binding of a large number of detector agents within the amplification unit. This final amplification step is represented schematically in FIG. 14.

Figure 13:
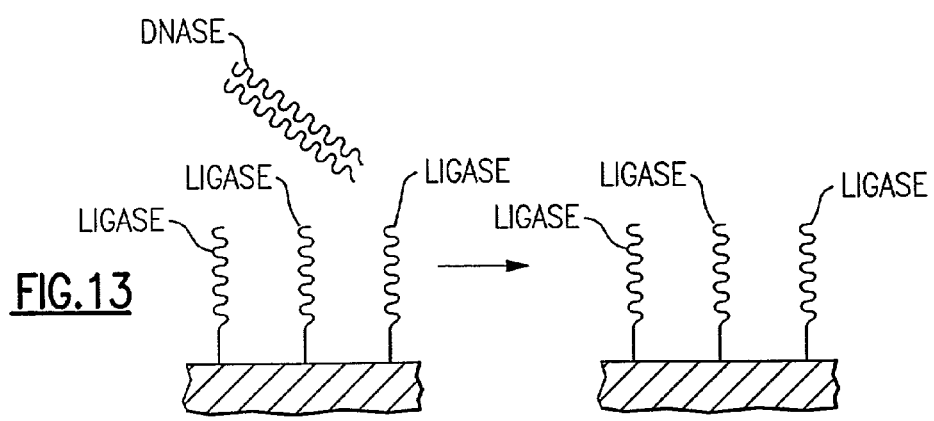
FIG. 13 is a diagrammatic representation of an amplification unit as described to FIGS. 11A–11D.
Figure 14:
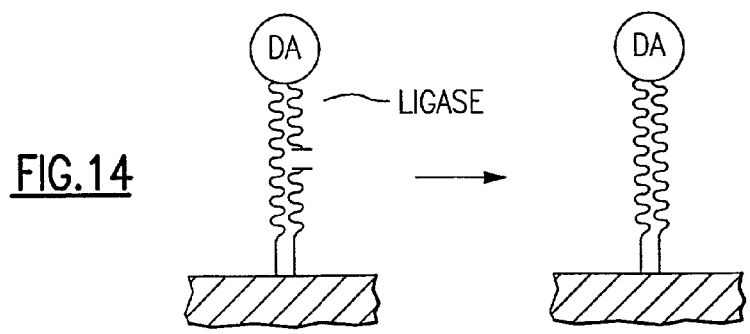
FIG. 14 is a diagrammatic representation of an amplification unit in accordance with the detection system shown in FIGS. 11A–11D.
Figure 15:
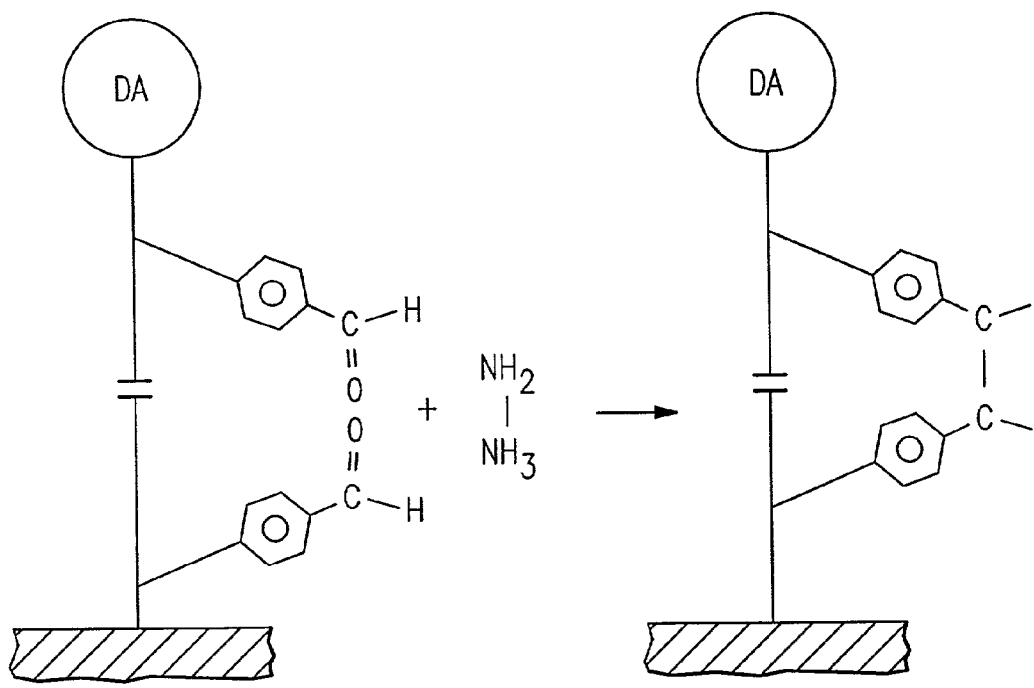
FIG. 15 shows an alternate embodiment of a cleavable detection agent.

In FIG. 13, the multiplier agent is a ligase. Other multiplier agents are possible which are not enzymatic or catalytic. For example, the ligase in FIG. 13 can be replaced with any compound which is capable of either cleaving or securing the bond between the detection agent and the disk in the amplification unit 124. Exemplary compounds include diamines or other compounds which are capable of converting an open bond to a covalent bond. FIG. 15 shows an exemplary detector agent wherein the bond between the detector agent can be easily cleaved. However, a diamine functioning as a multiplier agent will interact with the detection agent to securely bind it to the disk surface as shown in FIG. 15.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

What is claimed is:

1. An optical bio-disc for measuring the presence of an analyte in a sample, said bio-disc comprising:
   a first chamber comprising amplification agents bound to a first surface by first reversible bonds, wherein said first reversible bonds are configured to be broken when said amplification agents are contacted by said analyte;
   a second chamber fluidly connected to said first chamber and comprising detection agents bound to a second surface by second reversible bonds, wherein the strength of the second reversible bonds are altered upon contact by said amplification agents; and
   wherein a single amplification agent is adapted to alter the strength of more than one of said second reversible bonds, and wherein altering the strength of said second reversible bonds results in a change from a negative to a positive detection state of said detection agents indicating the presence of said analyte.

2. An optical disk-based detection system according to claim 1, wherein said first reversible bonds comprise DNA.

3. An optical disk-based detection system according to claim 1, wherein said second reversible bonds comprise DNA.

4. An optical disk-based detection system according to claim 1, wherein said single amplification reagent is adapted to break said second reversible bonds and release said detection agents in order to indicate the presence of said analyte.

5. An optical disk-based detection system according to claim 1, wherein said single amplification reagent is adapted to strengthen said second reversible bonds to prevent release of said detection agents in order to indicate the presence of said analyte.

6. An optical disk-based detection system according to claim 1, wherein said amplification agents comprise DNA ligase.

7. An optical disk-based detection system according to claim 6, wherein said analyte comprises a target DNA molecule and said amplification agents comprise DNA ligase linked to a DNA segment capable of hybridizing to said analyte.

8. An optical disk-based detection system according to claim 7, wherein said second reversible bonds comprise nicked DNA, and wherein said DNA ligase is capable of repairing said nicked DNA in order to strengthen said second reversible bonds.

* * * * *